(12) United States Patent
Plechinger et al.

(10) Patent No.: US 11,428,627 B2
(45) Date of Patent: Aug. 30, 2022

(54) SENSOR DEVICE

(71) Applicant: OSRAM Opto Semiconductors GmbH, Regensburg (DE)

(72) Inventors: Gerd Plechinger, Regensburg (DE); Tim Boescke, Regensburg (DE); Wolfgang Zinkl, Tegernheim (DE)

(73) Assignee: OSRAM OPTO SEMICONDUCTORS GMBH, Regensburg (DE)

( * ) Notice: Subject to any disclaimer, the term of this patent is extended or adjusted under 35 U.S.C. 154(b) by 0 days.

(21) Appl. No.: 17/279,514

(22) PCT Filed: Sep. 20, 2019

(86) PCT No.: PCT/EP2019/075318
§ 371 (c)(1),
(2) Date: Mar. 24, 2021

(87) PCT Pub. No.: WO2020/064541
PCT Pub. Date: Apr. 2, 2020

(65) Prior Publication Data
US 2021/0349016 A1    Nov. 11, 2021

(30) Foreign Application Priority Data

Sep. 25, 2018    (DE) .......................... 102018123559.3

(51) Int. Cl.
*G01N 21/3554*    (2014.01)

(52) U.S. Cl.
CPC ... *G01N 21/3554* (2013.01); *G01N 2201/062* (2013.01)

(58) Field of Classification Search
CPC .................... G01N 21/3554; G01N 2201/062
See application file for complete search history.

(56) References Cited

U.S. PATENT DOCUMENTS 10,750,984 B2 *  8/2020  Pauley .................. G01J 1/1626
2009/0318908 A1 * 12/2009  Van Pieterson ........ A61B 5/443
606/9

* cited by examiner

*Primary Examiner* — David P Porta
*Assistant Examiner* — Fani Polyzos Boosalis
(74) *Attorney, Agent, or Firm* — Slater Matsil, LLP (57) ABSTRACT

In an embodiment a sensor device includes a first optoelectronic emitter configured to irradiate a spot with electromagnetic rays, a second optoelectronic emitter configured to irradiate the spot with electromagnetic rays, a detector configured to detect electromagnetic rays from the first and second emitters reflected at or transmitted through the spot, wherein the electromagnetic rays of the first emitter have a wavelength in a range of 1400-1500 nm, wherein the electromagnetic rays of the second emitter have a wavelength in a range of 900-1100 nm, and wherein the second emitter is configured to emit at least one further electromagnetic signal, the one further electromagnetic signal not being used for measuring a humidity.

18 Claims, 3 Drawing Sheets

SENSOR DEVICE

This patent application is a national phase filing under section 371 of PCT/EP2019/075318, filed Sep. 20, 2019, which claims the priority of German patent application 10 2018 123 559.3, filed Sep. 25, 2018, each of which is incorporated herein by reference in its entirety.

TECHNICAL FIELD

The present invention relates to a sensor device, in particular for measuring humidity.

BACKGROUND

Conventional sensor devices, such as those used in sports watches, are suitable for measuring various vital parameters, such as pulse, heart rate, or blood oxygen saturation and/or other measurements that allow monitoring of human bodily functions. Such sensor devices typically include at least one emitter and one detector. The emitter, for example, in the form of an LED, thereby irradiates the skin surface of a user with electromagnetic rays, which are partly absorbed by the skin and partly reflected by it. The reflected electromagnetic rays are then detected by the detector and finally evaluated.

SUMMARY

Embodiments provide a reliable sensor device which, among other things, is suitable for measuring humidity and can be manufactured at low cost.

A sensor device according to embodiments, in particular for measuring humidity, comprises a first optoelectronic emitter, in particular an LED, for irradiating a spot with electromagnetic rays, a second optoelectronic emitter, in particular an LED, for irradiating the spot with electromagnetic rays, and a detector for detecting electromagnetic rays of the first and second emitter reflected at the spot or alternatively transmitted through the spot, wherein the first emitter emits electromagnetic rays at a wavelength in the range of 1400-1500 nm, and wherein the second emitter emits electromagnetic rays at a wavelength in the range of 900-1100 nm.

By providing two optoelectronic emitters emitting electromagnetic rays in two different wavelength ranges, respectively between 1400-1500 nm and 900-1100 nm, and a detector capable of detecting the electromagnetic rays from the two emitters, a particularly reliable sensor device suitable for moisture measurements is formed.

The approach to realize such a sensor device is based on optical properties of water. The optoelectronic emitters of the present sensor device are designed in such a way that the first emitter can emit electromagnetic rays at a wavelength in the range of 1400-1500 nm, preferably at least approximately 1450 nm. In this range, water has a local absorption maximum. The local absorption maximum is caused by an absorption band of water at a wavelength of 1470 nm, at which water molecules perform a combined stretching and bending vibration.

Instead, the second optoelectronic emitter is designed to emit electromagnetic rays at a wavelength in the range of 900-1100 nm, preferably in the range of 940-1070 nm, more preferably in the range of 940-1050 nm. In these IR spectral ranges of the second emitter, water has only a minor influence on the absorption and reflection or transmission of the electromagnetic rays. This makes the two emitters particularly suitable for measuring moisture at a single spot.

The two optoelectronic emitters can each be designed as light-emitting diodes (LEDs). Thus, an energy-efficient irradiation of a spot with electromagnetic rays can be achieved. The spot to be irradiated can be located outside the sensor device, e.g. outside a housing of the sensor device, for example on the skin surface of a user using the sensor device, on a section of a material, such as leather, or in a free space.

The two emitters can be configured in such that they emit the electromagnetic rays in a time-shifted manner, so that the detector only detects rays from one emitter at a time. In this way, it can be achieved that the two emitters emit at least one pulse of electromagnetic radiation with a time offset to each other or alternately.

This ensures that the rays from the two emitters enter the detector separately and do not cause signal distortion.

Furthermore, the time-shifted emission of the two emitters relative to each other allows the use of a single detector that can detect IR radiation in the 1400-1500 nm range as well as in the 900-1100 nm range. Replacing two separate detectors with only one detector leads to a reduction in the manufacturing cost of the sensor device. In addition, the external dimensions of the sensor device can be reduced. The sensor device can thus be more compact.

In particular, the present detector can be used to detect at least one further electromagnetic signal which does not originate from the first or second emitter. Thus, several parameters can be detected by means of only one detector.

The first emitter can be formed as an LED, which has an indium gallium arsenide layer (InGaAs) on an indium phosphide layer (InP). In this case, the active layer consists of or comprises the InGaAS, while InP is used as the substrate. Thus, the emitter enables energy-efficient emission of electromagnetic rays with a wavelength from a predefined long-wave IR spectral range.

Preferably, by using an InGaAs-based LED as emitter, which is built on an InP substrate, an emission of IR rays at a wavelength in the range of 1400-1500 nm, in which water has a very high absorption and a low reflection or transmission, can be achieved. Therefore, such an InGaAs-based LED is particularly suitable as an emitter for irradiating a spot, e.g. on a skin surface, for the purpose of moisture measurement.

The second emitter can be formed as an LED having an indium gallium arsenide (InGaAs) layer on an aluminum gallium arsenide (AlGaAs) substrate or on a gallium arsenide (GaAs) substrate. In this case, the active layer consists of or comprises the InGaAs, while AlGaAs or GaAs is used as the substrate. Such an AlGaAs- or GaAs-based LED can be used to irradiate a spot, in particular on a wet skin surface, with shorter-wavelength IR rays, for example in the range of 900-1100 nm, which are hardly absorbed and reflected by water. This makes the AlGaAs- or GaAs-based LED particularly suitable as a reference LED for verifying the moisture value of the irradiated spot determined by means of the first emitter.

Such an AlGaAs- or GaAs-based LED used as a second emitter may further be characterized by very high optical performance and efficiency. Providing an LED with an active layer of InGaAs on an AlGaAs or GaAs substrate in a sensor device can thus increase the sensitivity of the device and additionally be associated with a significant cost saving.

Such an LED of the sensor device used as a second emitter can be used to emit at least one further electromagnetic signal which is not used to measure moisture. Thus, the LED used as a second emitter can be used as an optical source for measuring further parameters, such as a pulse or oxygen content measurement, in particular on or in the skin surface of a user. Thus, a further emitter, in particular in the form of a reference LED, can be dispensed with. Thus, in addition to a cost reduction, a multifunctionality of the sensor device can be achieved in a small space.

The detector of the sensor device can be designed as a photodiode. The photodiode can provide reliable and cost-effective detection of the IR rays emitted by the two emitters.

The photodiode can have an indium gallium arsenide (InGaAs) layer on an indium phosphide (InP) layer. An InGaAs-based photodiode on an InP substrate has a very high sensitivity in the infrared range and is thus particularly well suited as a detector for detecting radiation from the IR ranges of the first and second emitters.

In addition, an InGaAs-based LED has a small dark current and a fast response time. This makes it particularly suitable as a detector for the reliable determination of rapidly changing parameters, especially for moisture measurement, e.g. on the skin surface.

A sensor device according to embodiments may further comprise a housing having a first cavity open to a bottom side of the housing and a second cavity open to the bottom side, wherein the two cavities are separated from each other, wherein in the first cavity the two emitters are arranged adjacent to each other, and wherein in the second cavity the detector is arranged. Such a design of the housing with two separate cavities or chambers ensures that the two emitters are spatially separated from the detector. This can reduce or prevent unwanted "cross talk" between the electromagnetic rays emitted by the two emitters and the rays received by the detector.

The term "bottom side" is used here to refer to that surface side of the housing which, in the position of use of the sensor device, faces the spot to be measured, e.g. the skin of a user. Ultimately, the orientation of the sensor device in space is arbitrary, so that the term bottom side is ultimately also arbitrary. In the accompanying drawings, for example, the bottom side can also point upwards.

By forming openings on the bottom side of the housing, which are assigned to each cavity, it can be achieved that the electromagnetic rays of the two emitters can efficiently reach the outside, i.e. outside of the sensor device, in particular onto the spot to be measured, from the cavity in which they are arranged. Furthermore, such a design of the housing also allows the rays reflected from the outside, e.g. at the spot, or transmitted through the spot, to enter the cavity of the detector and be detected.

Each of the two cavities can further have a top side opposite the bottom side of the housing and a circumferential side separation extending between the bottom and the bottom side of the housing, preferably in the form of a wall or bar.

In particular, the two emitters can be arranged adjacent to each other in a cavity. In a further embodiment of the sensor devices disclosed herein, each of the two emitters can be arranged in a separate cavity. Each of the cavities can thereby have an opening arranged on the bottom side of the housing.

The bottom of the housing can have a cover that covers the cavities. The cover can be completely or at least partially transparent to the radiation emitted by the two emitters and the radiation received by the detector.

A sensor device according to embodiments can comprise an evaluation device which is designed to determine at least one measured value, in particular for a humidity at the spot, as a function of the detected electromagnetic rays of the two emitters. For this purpose, the portion of the electromagnetic rays of the two emitters reflected from or transmitted through the spot is detected by the detector as a separate signal in each case. A direct comparison of the two signals can be made by means of the evaluation device. A mathematical function can be implemented in the evaluation device, for example by means of software, by means of which a variable characterizing the moisture at the skin spot can be calculated as a function of the measured values determined.

In particular, the evaluation device can precisely evaluate a parameter, in particular determine a degree of moisture of a spot, by relating the signal originating from the first emitter to the signal of the second emitter. Via the reference signal obtained by means of the second emitter, a comparison of the proportion of reflected or transmitted rays is possible. Thus, the evaluation device can be used for the precise determination of at least one measured value, in particular the degree of moisture of the spot outside the sensor device, e.g. on a skin surface.

The evaluation device can be designed as a circuit. The circuit can be connected to the two emitters and/or the detector. The evaluation device can further be arranged in the same cavity as the detector or in a further cavity which is also closed with a cover, preferably detachably. The evaluation device can be arranged, for example, on the top side of the housing.

Further embodiments relate to a sensor device, in particular for measuring humidity, wherein the sensor device comprises:

a first optoelectronic emitter, in particular an LED, for irradiating a spot with electromagnetic rays, a second optoelectronic emitter, in particular an LED, for irradiating the spot with electromagnetic rays, wherein the first optoelectronic emitter is operable to detect at least a portion of electromagnetic rays from the second emitter that has been reflected at the spot or alternatively transmitted through the spot, and wherein the second optoelectronic emitter is operable to detect at least a portion of electromagnetic rays from the first emitter that has been reflected at the spot or alternatively transmitted through the spot.

Preferably, the two emitters enable efficient irradiation of a spot with electromagnetic rays of a wavelength from at least one respective, predefined spectral range. In this context, the spot can be, for example, outside the sensor device, in particular on a skin surface or in a room.

Because each of the two emitters is configured to detect a portion of the electromagnetic rays from the other emitter, the two emitters are suitable for detecting the radiation reflected at or transmitted through the spot. The detection capability of the two emitters eliminates the need for additional detectors in the sensing device, resulting in space and cost savings.

The electromagnetic radiation of one emitter can be detected by the respective other emitter by means of a photocurrent measurement. The respective emitter serving as a detector can be operated in a detection mode. For example, an LED can be operated as a photodiode for the purpose of detection and the detected radiation can be detected by means of a photocurrent.

The two emitters can be operated time-shifted as emitter and detector respectively, so that each of the two emitters can temporarily detect at least a portion of the electromagnetic rays emitted by the other emitter. In this way, it can be achieved that the two emitters emit in a time-shifted way with respect to each other or alternatively at least one pulse of electromagnetic radiation each, which irradiates one spot and can subsequently be detected at least partially by the other emitter.

Depending on the arrangement of the two emitters relative to each other, one emitter can detect either the rays reflected at the spot or the rays transmitted through the spot, of the respective other emitter.

Preferably, the first emitter can emit electromagnetic rays at a wavelength in the range of 1450 nm or greater. Preferably, the second emitter can emit electromagnetic rays at a wavelength in the range of 1450 nm or smaller. By means of the two emitters, in particular two LEDs, an emission of electromagnetic rays with a wavelength from two different, predefined IR spectral ranges can take place. In particular, the first emitter is configured to emit electromagnetic rays at a wavelength at which water has a local absorption maximum and is characterized by very low reflection or transmission. In contrast, the second emitter is preferably configured to emit electromagnetic rays at a wavelength at which water has hardly any influence on the reflection or transmission of the emitted rays. Thus, the two emitters are particularly suitable for moisture measurement in a sensor device.

The fact that the two emitters can be operated as detectors time-shifted means that one emitter can detect at least a portion of the emission spectrum of the other emitter. The first emitter, which emits electromagnetic rays in a longwave IR spectral range, can detect the complete emission spectrum of the second emitter, which falls entirely within its absorption range.

The shorter wavelength second emitter is configured in such that it can absorb electromagnetic radiation from the longer wavelength first emitter, especially at its peak wavelength. Detection of electromagnetic rays originating from the first emitter by the second emitter is thus possible.

The two emitters can thus be selected or designed such that there is an overlap between the emission spectrum of the first emitter and the absorption spectrum of the second emitter. This may allow the second emitter, which emits electromagnetic rays in a shorter wavelength IR spectral region, to at least partially detect the emission spectrum of the first emitter. In particular, this overlapping region of the two emitters' spectral ranges can coincide with the IR spectral range in which water has an absorption maximum. Thus, it can be achieved that a water content of a spot to be irradiated, in particular on a skin surface, has a maximum influence on the electromagnetic rays of the first emitter partially detected by the second emitter.

Furthermore, the emission spectrum of the second emitter, in particular a reference LED, can be selected such that it has an overlap with the wavelength range that can be maximally absorbed by water at the spot to be irradiated. In the overlap range, the water content already has a great influence. However, when the influence of the water content is considered in relation to the complete emission spectrum of the second emitter, it can be assumed to be small. Because the complete emission spectrum of the second emitter can be detected by the first emitter, the detected electromagnetic rays are negligibly influenced by the water content of the spot. Thus, the second emitter is particularly suitable as a reference LED for measuring moisture, e.g. on a skin surface, in a sensor device.

The sensor device can also comprise an evaluation device which is designed to determine at least one measured value, in particular for moisture at the spot, as a function of the electromagnetic rays of the respective other emitter detected by the two emitters. For this purpose, the portion of the electromagnetic rays of the respective emitter reflected at a spot or alternatively transmitted through the spot is detected as a separate signal by the respective other emitter used as a detector.

In particular, the evaluation device can determine a degree of moisture at a spot by relating the signal originating from the first emitter, in particular an LED, to the signal from the second emitter, in particular the reference LED. Thus, the evaluation device can be used to precisely determine at least one measured value, in particular a degree of moisture of a spot outside the sensor device, for example on or in a skin surface.

The evaluation device can be designed as a circuit. The circuit can be connected to the two emitters.

The two emitters can be LEDs that have an indium gallium arsenide (InGaAs) layer on top of an indium phosphide (InP) layer.

Preferably, by using InGaAs-based LEDs on an InP substrate, emission of electromagnetic rays can be achieved at a wavelength in different IR spectral regions where water has very high or very low absorption. In addition, InGaAs-based detectors comprise a very high sensitivity in the infrared region. As a result, InGaAs-based LEDs can be used both as emitters and detectors to detect electromagnetic radiation from diverse IR ranges, in particular to measure moisture at a spot. This eliminates the need for additional detectors, e.g. in the form of a separate photodiode.

The sensor device can further comprise a housing having a first cavity open to a bottom side of the housing and a second cavity open to the bottom side, wherein the two cavities are separated from each other, and wherein the first emitter is arranged in the first cavity and the second emitter is arranged in the second cavity. By designing the housing with two separate cavities, it can be ensured that the first emitter is spatially separated from the second emitter. This means that undesirable "cross talk" between the electromagnetic rays emitted and detected by the two emitters respectively can be ruled out.

By forming openings on the bottom side of the housing, which are assigned to each cavity, it can be achieved that the electromagnetic rays of the two emitters can efficiently reach the outside, i.e. outside the sensor device, in particular a spot to be irradiated, from the respective cavity in which they are arranged. Furthermore, the electromagnetic rays reflected from outside, e.g. from the spot, or alternatively transmitted through the spot, can also reach the cavity of the respective emitter operated as a detector.

Each of the two cavities can further comprise a top side opposite the bottom side of the housing and a circumferential side separation extending between the bottom and the bottom side of the housing, preferably in the form of a wall or bar.

The bottom side of the housing can comprise a cover that is at least partially transparent to the rays of the two emitters. The cover can serve as a preferably detachable closure of the cavities.

The sensor device can be configured to measure skin moisture by applying a housing of the sensor device to the skin surface of a user such that the emitted electromagnetic rays can be irradiated onto or into a skin spot of the user and rays reflected from that skin spot can be detected.

Embodiments also relate to a wearable electronic device, in particular a fitness watch or an activity tracker, with a sensor device according to embodiments and an attachment device connected to the sensor device for attaching the sensor device to a body part of the user, in particular in such a way that the bottom side of the sensor device faces the body part and/or is in direct contact with the body part.

The sensor devices disclosed herein can be integrated into a wearable electronic device, such as an activity or fitness tracker or smartwatch. The housing of the sensor device can correspond to or be integrated into the housing of the device. The housing can be connected to a wristband or strap to attach the device to a body part of a user, in particular such that the bottom side of the sensor device, or the cover disposed thereon, rests against the body part. The sensor device can further be a component of a mobile phone. It can be used, for example, as a moisture measurement sensor, in particular as a skin moisture measurement sensor.

Yet further embodiments relate to a method for operating the sensor device according to embodiments, the method comprising the following steps:

(a) bringing a housing of the sensing device into contact with a skin spot of a user;

b) successively irradiating the skin spot with electromagnetic rays from the two emitters;

c) successively detecting the electromagnetic rays reflected from the skin spot by the two emitters; and d) determining a moisture level as a function of the detected electromagnetic rays.

The two emitters are thus not actuated simultaneously to emit electromagnetic radiation, but successively. A pulse emitted by a respective emitter and reflected by the skin spot is detected. The detection can be done either by a separate detector or by the other emitter.

BRIEF DESCRIPTION OF THE DRAWINGS

The invention is explained in more detail below by means of examples of embodiments.

DETAILED DESCRIPTION OF ILLUSTRATIVE EMBODIMENTS

Figure 1:
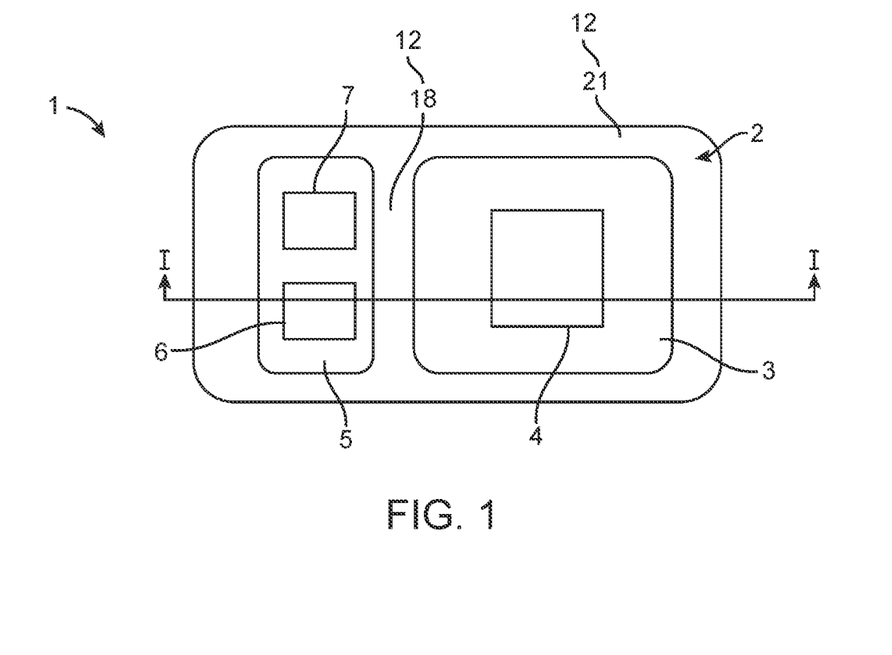
FIG. 1 shows a perspective view of a sensor device according to embodiments in accordance with a first embodiment, including two emitters and a detector.

The sensor device 1 shown in FIG. 1 is particularly suitable for measuring moisture, for example, at a spot on the skin surface of a user. It comprises two emitters, a first emitter 6 and a second emitter 7, and a detector 4.

The two emitters 6 and 7 are designed as optoelectronic emitters, in particular as LEDs, and are used to irradiate the spot with electromagnetic rays. In particular, the first emitter 6 can be an InGaAs/InP-based LED. The second emitter 7 can be formed as an InGaAs/AlGaAs-based or an InGaAs/GaAs-based LED. Thus, in the first emitter 6, the active layer comprises InGaAs and the substrate is InP. In the second emitter 7, the active layer comprises InGaAs on an AlGaAs substrate or a GaAs substrate.

In particular, the first emitter 6 can emit electromagnetic rays at a wavelength in the range of 1400-1500 nm, preferably at least approximately 1450 nm, while the second emitter 7 can emit electromagnetic rays at a wavelength in the range of 900-1100 nm, preferably in the range of 940-1070 nm, more preferably in the range of 940-1050 nm.

The detector 4 can be designed as an InGaAs/InP-based photodiode. It is used to detect electromagnetic rays from the first and second emitters 6, 7 that are reflected at the irradiated spot. In the photodiode, the active layer thus consists of InGaAs arranged on an InP substrate.

As shown in FIG. 1, the two emitters 6 and 7 are arranged in a first cavity 5 of a housing 2 of the sensor device 1, while the detector 4 is arranged in a second cavity 3 of the housing 2. The two cavities 3 and 5 are arranged adjacent to each other in a longitudinal direction of the housing 2. Thereby, the two cavities 3 and 5 are separated from each other by a partition 18. The cavity 5 is formed, for example, as an elongated rectangle with rounded corners. It extends in a transverse direction of the housing 2. The cavity 3 has a substantially square basic shape with, for example, rounded corners. The two emitters 6, 7 are spaced apart from each other and arranged along a longitudinal direction of the cavity 5. In the example shown, the two cavities 3, 5 are of equal width (cf. the direction perpendicular to the line of intersection I-I). However, different widths and lengths are also possible for the cavities 3, 5.

Figure 2:
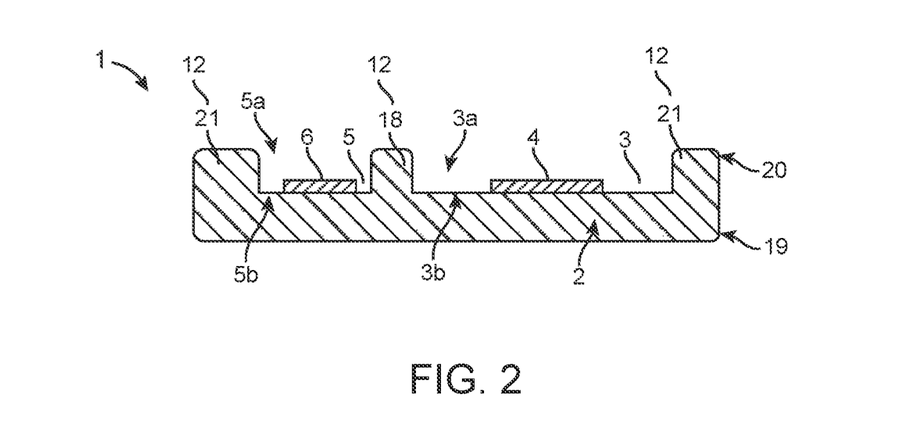
FIG. 2 shows a perspective view of the sensor device of FIG. 1, cut along the line of intersection I-I.

As it can be seen from FIG. 2, the housing 2 of the sensor device 1 has a top side 19, a bottom side 20, and a circumferential outer wall 21 extending between the top side 19 and the bottom side 20 of the housing 2.

Each of the cavities 3, 5 has a bottom 3b, 5b arranged on the upper side 19 of the housing 2, as well as an opening 3a, 5a associated with the bottom side 20 of the housing 2 (cf. FIG. 2). Thus, each of the two cavities 3, 5 is open towards the bottom side 20 of the housing 2. Thus, electromagnetic radiation from the two emitters 6, 7 can pass out of the cavity 5. The radiation can therefore leave the housing 2 and reach a spot to be irradiated. However, a cover transparent to the radiation may be arranged over the cavities 3, 5 to close them. Furthermore, the radiation reflected from the two emitters 6, 7 at the spot can enter the second cavity 3 of the detector 4 to be detected there. Each of the two cavities 3, 5 further has a side wall 12 enclosing the bottom 3b, 5b, which is formed by the outer wall 21 and the partition 18 of the housing 2 (FIGS. 1, 2).

Figure 3:
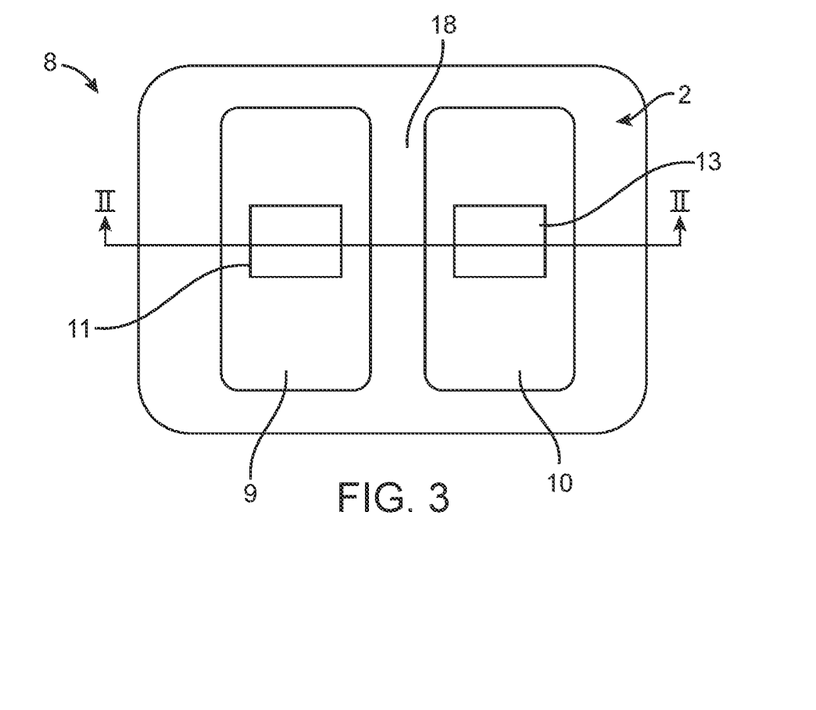
FIG. 3 shows a perspective view of a sensor device according to embodiments in accordance with a second embodiment, including two emitters.

The sensor device 8 shown in FIG. 3 differs from the sensor device 1 of FIGS. 1-2 substantially in that it comprises two optoelectronic emitters, namely a first emitter 11 and a second emitter 13, but no additional detector.

The two emitters 11, 13 of the sensor device 8 can, for example, be designed as LEDs and, like the emitters 6, 7 of the sensor device 1, are used to irradiate a spot with electromagnetic rays, in particular on the skin surface of a user.

For the purpose of measuring moisture at the spot, each of the two emitters 11, 13 is operated as a detector with a time offset, while the respective other emitter 11, 13 is used as an emitter. Thereby, each of the two emitters 11, 13 can detect at least a portion of the electromagnetic rays of the respective other emitter 11, 13, which were reflected at the irradiated spot.

The emitters 11, 13 can be designed as InGaAs/InP-based LEDs. In this context, the first emitter 11 can emit electromagnetic rays at a wavelength in the IR spectral range of 1450 nm and more. Further, the second emitter 13 can emit, in particular, IR rays at a wavelength in the range of less than 1450 nm. In particular, the shorter wavelength, second emitter 13 is designed to absorb electromagnetic radiation from the longer wavelength, first emitter 11, especially at its peak wavelength. Detection of electromagnetic rays originating from the first emitter 11 by the second emitter 13 is therefore possible.

As shown in FIG. 3, the two emitters 11, 13 are arranged in a housing 2 of the sensor device 8 in such a way that each emitter 11, 13 is positioned in a separate cavity 9, 10 respectively. The two cavities 9, 10 are arranged side by side in a longitudinal direction of the housing 2. Thereby, they are separated from each other by a partition 18. The two cavities 9, 10 are each formed as elongated rectangular recesses with rounded corners extending parallel to each other and transversely to a longitudinal direction of the housing 2. Other configurations of the cavities 9, 10 are also conceivable which do not impair the functionality of the emitters 11, 13 and of the detector 4 and allow maximum decoupling of the emission rays.

Figure 4:
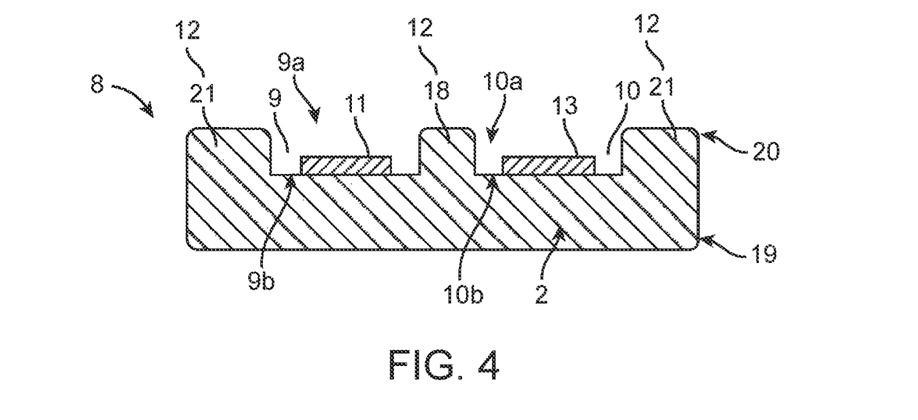
FIG. 4 shows a perspective view of the sensor device of FIG. 3, cut along section line II-II.
Figure 5:
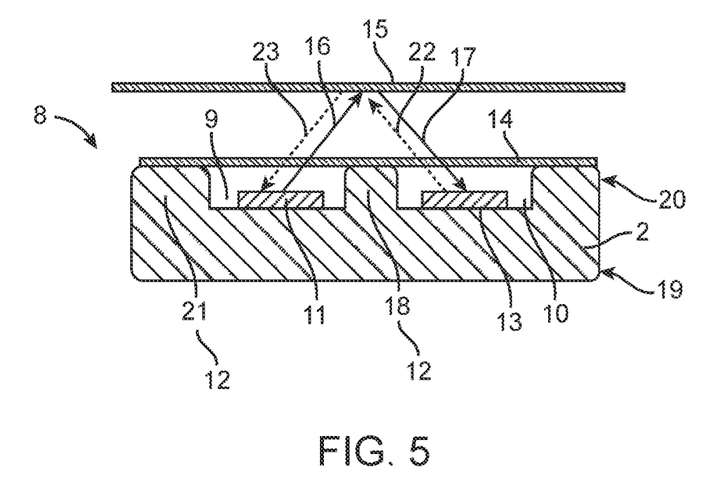
FIG. 5 shows a perspective view of the sensor device of FIG. 3 with a cover transparent to electromagnetic rays from the two emitters.

The housing 2 of the sensor device 8 also has, like the housing 2 of the sensor device 1 of FIGS. 1, 2, a top side 19, a bottom side 20, and a partition 18 separating the two cavities 9, 10 from each other (see FIGS. 4, 5). Furthermore, similar to the cavities 3, 5 already described, the cavities 9, 10 are each provided with an opening 9a, boa arranged at the bottom side 20 of the housing 2. Through the openings 9a, 10a, the IR radiation of each one emitter 11, 13 can reach the outside, i.e. outside the housing 2, from one of the two cavities 9, 10 time-shifted, onto a spot to be irradiated. Afterwards, the reflected radiation can enter the respective other cavity 9, 10 for the purpose of detection. The cavities 9, 10 can in turn be covered by a cover that is transparent to the radiation.

In addition, the cavities 9, 10 each comprise a bottom 9b, 10b arranged on the top side 19 of the housing 2 and an enclosing side wall 12 formed by the outer wall 21 and the partition 18 of the housing 2 (FIG. 4).

As has already been mentioned and is exemplified in FIG. 5 in connection with the sensor device 8, the housing 2 of the sensor devices 1, 8 disclosed herein may further comprise a cover 14.

The cover 14 shown in FIG. 5 is arranged on the bottom side 20 of the housing 2 and is at least partially transparent to the IR rays emitted and detected by the two emitters 11, 13.

FIG. 5 further shows how the sensor device 8 can be used, for example for the purpose of measuring humidity. For this purpose, the sensor device 8, which is integrated, for example, in a fitness watch, an activity tracker, a cell phone or another electronic device, is brought with the cover 14 arranged on the bottom side 20 into close proximity or directly onto a spot 15 to be measured, in particular onto the skin surface of a user. By means of the two emitters 11, 13, which may for example be LEDs, electromagnetic radiation is alternately irradiated onto the spot 15. Exemplary emission rays of the two emitters 11, 13 are shown in FIG. 5 and are respectively marked with the reference signs 16 and 22. The emission rays 16, 22 are absorbed and partially reflected at the spot 15 in a wavelength-dependent manner, so that a portion of the rays (referenced as rays 17, 23) passes via the transparent cover 14 into the respective other cavity 9, 10 in order to be detected there by the respective other emitter 11, 13. The proportion of reflected rays 17, 23 varies, for example, as a function of a degree of humidity of the irradiated spot. This variation can be detected by the emitter 11, 13 used as a detector and further evaluated by means of an evaluation device (not shown). The evaluation device is designed to determine at least one measured value, in particular a degree of moisture or another variable characterizing the skin moisture, as a function of the detected rays 17, 23 of the two emitters 11, 13.

The functionality of the sensor device 8 corresponds substantially to the functionality of the sensor device 1 of FIGS. 1 and 2, with the difference that in the sensor device 1 the detection is carried out by means of a separate detector 4. Thus, the emission rays 16 of the emitter 11 shown in FIG. 5, correspond to the emission rays of the two emitters 6, 7 of the sensor device 1 of FIGS. 1, 2, which can be operated time-shifted, while the rays 17 reflected at the spot 15 (FIG. 5), correspond to the rays detected by the detector 4 of the sensor device 1.

Figure 6:
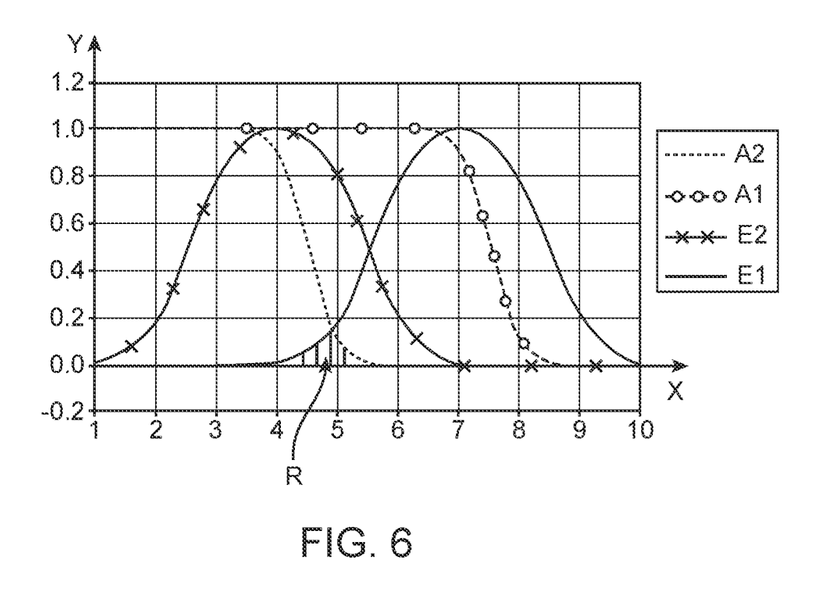
FIG. 6 shows emission and absorption spectra of the two emitters of the sensor device of FIGS. 3-5.

FIG. 6 shows a relationship between the emission and absorption spectra of the two emitters 11, 13 of the sensor device 8 of FIGS. 3-5. The horizontal X-axis of the diagram shown in FIG. 6 denotes the wavelength of the electromagnetic rays emitted or detected by the emitters 11, 13 in arbitrary units (w.E.). The vertical Y-axis shows absorption or emission values of the two emitters 11, 13, which are also given in arbitrary units.

The line (E1) denotes the emission spectrum of the first emitter 11, which is configured, for example, to emit electromagnetic rays in the IR spectral range of more than 1450 nm, preferably including 1450 nm. In this case, the emission spectrum of the first emitter 11 is in the range of 4-10 w.E. with an emission maximum (value 1) at a wavelength of 7 w.E. The crossed line (E2) shows the emission spectrum of the second emitter 13, which can emit, for example, electromagnetic rays in the IR spectral range of up to 1450 nm. The second emitter 13 shows the same emission maximum as the first emitter 11 (value 1), but at a wavelength of 4 w.E. in a spectral range of 1-7 w.E. The emission maxima can also differ from each other.

FIG. 6 also shows that the two emitters 11, 13 can be operated as detectors time-shifted. The dashed line (A1) with additional dots shows the absorption spectrum of the first emitter 11. The dashed line (A2) indicates the absorption spectrum of the second emitter 13.

The first emitter 11, used as a detector, can absorb electromagnetic radiation in a wavelength range of 1-8.5 w.E. In contrast, the second emitter 13 can detect radiation in a shorter wavelength spectral range of 1-5.5 w.E. Thus, the first emitter 11 can detect the complete emission spectrum (1-7.5 w.E.) of the second emitter 13. The second emitter 13 can detect a portion of the electromagnetic radiation emitted by the first emitter 11 that is at a wavelength in the range of 4 to 5.5 w. E. This is indicated by the dashed region R in FIG. 6. The two emitters 11, 13 can thus detect at least a portion of the spectrum of the radiation emitted by the respective other emitter 11, 13.

For the purpose of moisture measurement of the spot 15 to be irradiated, the wavelengths of the two emitters 11, 13 can be selected so that the overlap range (4 to 5,5 w.E.) of the emission spectrum (4-10 w.E.) of the first emitter 11 with the absorption spectrum (1-5,5 w.E.) of the second emitter 13 corresponds to a wavelength range in which water absorption at the spot 15 has a maximum. It is thus possible to perform a moisture measurement of a spot 15, e.g. a skin spot, by means of the two emitters 11, 13 and without an additional detector.

The case where reflected radiation is detected by the sensor device at a spot has been described above with reference to the figures. This case is particularly applicable when, in order to measure a skin moisture level, the sensor device is brought into contact with a skin spot of a user and a determination of the moisture level is made based on the reflected radiation, as previously described. In cases where the spot at which a measurement is made is on the surface of a user's skin, a transmission measurement does not make sense. However, in other cases, for example to measure moisture in the air, it might make sense to perform a transmission measurement instead of a reflection measurement. In this case, the rays transmitted through a spot could be measured and a degree of humidity determined on the basis of the detected signals.

The invention claimed is:

1. A sensor device comprising:
a first optoelectronic emitter configured to irradiate a spot with electromagnetic rays;
a second optoelectronic emitter configured to irradiate the spot with electromagnetic rays; and
a housing having a first cavity open to a bottom side of the housing and a second cavity open to the bottom side,
wherein the two cavities are separated from each other,
wherein the first emitter is arranged in the first cavity and the second emitter is arranged in the second cavity,
wherein the first optoelectronic emitter is configured to detect at least a portion of the electromagnetic rays from the second emitter that have been reflected at or transmitted through the spot,
wherein the second optoelectronic emitter is configured to detect at least a portion of electromagnetic rays from the first emitter that have been reflected at or transmitted through the spot,
wherein the electromagnetic rays of the first emitter have a wavelength in a range above 1450 nm,
wherein the electromagnetic rays of the second emitter have a wavelength in a range below 1450 nm,
wherein the second emitter is configured to detect at least a portion of a spectrum emitted by the first emitter, and
wherein the sensor device is configured to measure humidity.

2. The sensor device according to claim 1, wherein the two emitters are configured to be operated as emitter and detector in a time-shifted manner so that each of the two emitters is configured to temporarily detect at least a portion of the electromagnetic rays emitted by the other emitter.

3. The sensor device according to claim 1, wherein the two emitters are LEDs comprising an indium gallium arsenide (InGaAs) layer on an indium phosphide (InP) layer.

4. The sensor device according to claim 1, wherein the sensor device is configured to measure skin moisture, wherein the housing of the sensor device is applicable to a skin surface of a user such that the emitted electromagnetic rays are irradiatable into or onto a skin spot of the user and electromagnetic rays reflected from the skin spot are detectable.

5. A wearable electronic device comprising:
the sensor device according to claim 1; and
an attachment means for attaching the sensor device to a body part of a user,
wherein the attachment means is connected to the sensor device.

6. A method for operating the sensor device according to claim 1, the method comprising:
contacting the housing of the sensor device with a skin spot of a user;
irradiating the skin spot with the electromagnetic rays from the two emitters;
detecting the electromagnetic rays reflected from the skin spot by the two emitters; and
determining a moisture level as a function of the detected electromagnetic rays.

7. The sensor device according to claim 1, wherein the electromagnetic rays of the second emitter have a wavelength in a range of 900-1100 nm.

8. A sensor device for measuring humidity, the sensor device comprising:
a first optoelectronic emitter configured to irradiate a spot with electromagnetic rays;
a second optoelectronic emitter configured to irradiate the spot with electromagnetic rays;
a detector configured to detect electromagnetic rays from the first and second emitters reflected at or transmitted through the spot; and
a housing having a first cavity open to a bottom side of the housing and a second cavity open to the bottom side,
wherein the electromagnetic rays of the first emitter have a wavelength in a range of 1400-1500 nm,
wherein the electromagnetic rays of the second emitter have a wavelength in a range of 900-1100 nm,
wherein the second emitter is configured to emit at least one further electromagnetic signal, the one further electromagnetic signal not being used for measuring the humidity,
wherein the two cavities are separated from each other,
wherein the two emitters are arranged next to each other in the first cavity, and
wherein the detector is arranged in the second cavity.

9. The sensor device according to claim 8, wherein the two emitters are configured to emit the electromagnetic rays in a time-shifted manner so that the detector is able to detect only electromagnetic rays of one emitter at a time.

10. The sensor device according to claim 8, wherein the first emitter is an LED comprising an indium gallium arsenide layer (InGaAs layer) on an indium phosphide layer (InP layer).

11. The sensor device according to claim 8, wherein the second emitter is an LED comprising an indium gallium arsenide layer (InGaAs layer) on an aluminum gallium arsenide layer (AlGaAs layer) or on a gallium arsenide layer (GaAs layer).

12. The sensor device according to claim 8, wherein the detector is a photodiode.

13. The sensor device according to claim 12, wherein the photodiode comprises an indium gallium arsenide (InGaAs) layer on an indium phosphide (InP) layer.

14. The sensor device according to claim 8, wherein the bottom side comprises a cover which is at least partially transparent to the electromagnetic rays of the two emitters.

15. The sensor device according to claim 8, further comprising an evaluation device configured to determine the humidity at the spot as a function of the detected electromagnetic rays of the two emitters.

16. The sensor device according to claim 8, wherein the sensor device is configured to measure skin moisture, and wherein the housing of the sensor device is applicable to a skin surface of a user such that the emitted electromagnetic rays are irradiatable into or onto a skin spot of the user and electromagnetic rays reflected from the skin spot are detectable.

17. A wearable electronic device comprising:
the sensor device according to claim 8; and
an attachment means for attaching the sensor device to a body part of a user,
wherein the attachment means is connected to the sensor device.

18. A method for operating the sensor device according to claim 8, the method comprising:
   contacting the housing of the sensor device with a skin spot of a user;
   irradiating the skin spot with electromagnetic rays from the two emitters;
   detecting the electromagnetic rays reflected from the skin spot by the two emitters; and
   determining a moisture level as a function of the detected electromagnetic rays.

\* \* \* \* \*